United States Patent [19]
Brown et al.

[11] Patent Number: 5,899,902
[45] Date of Patent: * May 4, 1999

[54] FASTENER

[75] Inventors: Henry John Harding Brown, Solon; John Mark Kapitan, Shaker Hts.; Gerald Kotnik, Perry; Marcus Maria Sanders, Cleveland, all of Ohio

[73] Assignee: DePuy Motech AcroMed Corporation, Cleveland, Ohio

[*] Notice: This patent is subject to a terminal disclaimer.

[21] Appl. No.: 08/887,832

[22] Filed: Jul. 3, 1997

[51] Int. Cl.[6] ................................................. A61B 17/70
[52] U.S. Cl. ................................. 606/61; 606/73; 606/104
[58] Field of Search .................................. 606/61, 60, 72, 606/73, 104

[56] References Cited

U.S. PATENT DOCUMENTS

| | | |
|---|---|---|
| 4,269,246 | 5/1981 | Larson et al. . |
| 4,854,311 | 8/1989 | Steffee . |
| 5,019,080 | 5/1991 | Hemer ........................................... 606/73 |
| 5,024,213 | 6/1991 | Asher et al. . |
| 5,085,660 | 2/1992 | Lin ............................................. 606/73 |
| 5,129,900 | 7/1992 | Asher et al. . |
| 5,257,994 | 11/1993 | Lin . |
| 5,443,482 | 8/1995 | Stone et al. ............................ 606/232 |
| 5,454,811 | 10/1995 | Huebner .................................... 606/60 |
| 5,470,334 | 11/1995 | Ross et al. ................................ 606/72 |
| 5,613,968 | 3/1997 | Lin ............................................ 606/61 |
| 5,620,443 | 4/1997 | Gertzbein et al. ....................... 606/61 |
| 5,669,909 | 9/1997 | Zdeblick et al. ........................ 606/61 |

*Primary Examiner*—Guy V. Tucker
*Attorney, Agent, or Firm*—Barnes & Thornburg

[57] ABSTRACT

An improved fastener is provided for use in retaining vertebrae in a desired spatial relationship. The fastener has a mounting section with a first external thread to engage a vertebra. The fastener has a retaining section with a second external thread to engage an internal thread on a retaining element, such as a nut. A pair of parallel flats are formed on opposite sides of the retaining section. The flats are spaced apart by a distance which is substantially the same as or greater than a root diameter of the external thread on the retaining section. A driving recess in an axially outer end of the retaining section has arcuate corner portions which receive force to effect rotation of the fastener relative to a vertebra engaged by the mounting section. The arcuate corner portions of the driving recess are offset from a plane containing the longitudinal central axis of the retaining section and extending perpendicular to the flats.

15 Claims, 3 Drawing Sheets

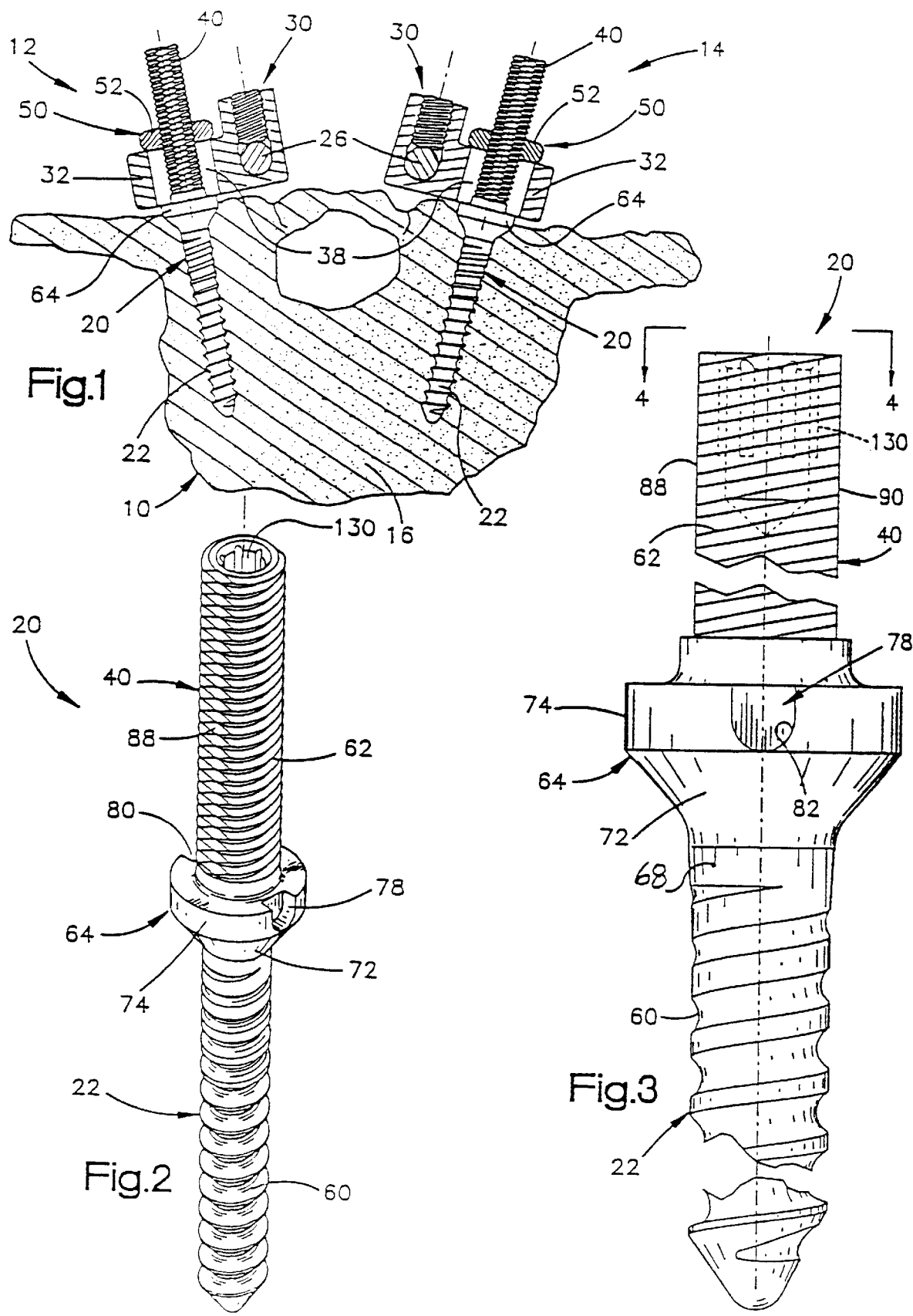

005,899,902

FASTENER

BACKGROUND OF THE INVENTION

The present invention relates to a new and improved fastener for use in retaining vertebrae in a desired spatial relationship.

Known fasteners have been used to retain vertebrae in a desired spatial relationship. At least one of these known fasteners has a mounting section with an external thread convolution which engages bone in a vertebra. This known fastener has a retaining section which extends axially outward from the mounting section. An external thread convolution is provided on the retaining section for engagement with an internally threaded retaining element, that is, a nut.

A hexagonal intermediate or head section is provided between the mounting and retaining sections of the known fastener. The intermediate section of the known fastener is engageable by a tool to rotate the fastener relative to a vertebra. A fastener having this construction is disclosed in U.S. Pat. No. 4,854,311. Other known fasteners which are used to retain vertebrae in a desired spatial relationship are disclosed in U.S. Pat. Nos. 5,085,660; 5,257,994; and 5,620,443.

SUMMARY OF THE INVENTION

The present invention provides a new and improved fastener to retain vertebrae in a desired spatial relationship. The fastener includes a mounting section having an external thread which engages a vertebra. The fastener has a retaining section. The retaining section may have a pair of parallel flats disposed on opposite sides of the retaining section. In addition, the retaining section may have a drive recess disposed between the flats at one end of the retaining section. The drive recess has a plurality of arcuate corner portions which are offset from a plane containing a longitudinal central axis of the retaining section and extending perpendicular to the flats.

An external thread may be provided around the retaining section to engage an internal thread on a retaining element. The flats on the retaining section may be spaced apart by a distance which is at least as great as a root diameter (minor diameter) of the external thread on the retaining section.

BRIEF DESCRIPTION OF THE DRAWINGS

The foregoing and other features of the present invention will become more apparent upon a consideration of the following description taken in connection with the accompanying drawings, wherein:

FIG. 1 is a simplified schematic illustration depicting the manner in which a pair of fasteners constructed in accordance with the present invention are connected with a vertebra in a spinal column;

FIG. 2 is an enlarged pictorial illustration of one of the fasteners of FIG. 1;

FIG. 3 is an enlarged fragmentary view of the fastener of FIG. 2;

DESCRIPTION OF SPECIFIC PREFERRED EMBODIMENT OF THE INVENTION

General Description

Figure 4:
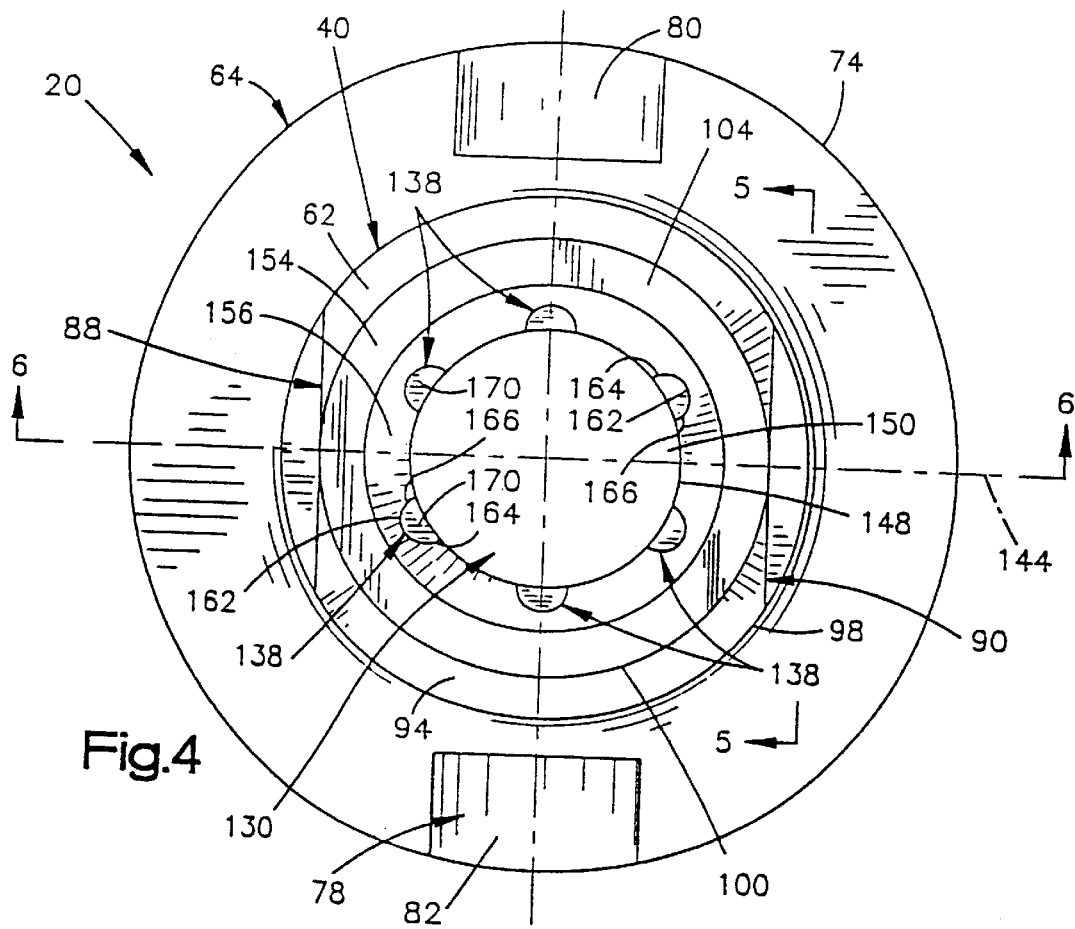
FIG. 4 is an end view, taken generally along the line 4—4 of FIG. 3, illustrating the construction of a retaining section and an intermediate section of the fastener of FIG. 2.

A human spinal column 10 to which a pair of retainer assemblies 12 and 14 are connected is illustrated in FIG. 1. The retainer assemblies 12 and 14 retain portions of the spinal column, that is vertebrae 16 in a desired spatial relationship relative to each other.

The retainer assemblies 12 and 14 have the same construction and include fasteners 20 constructed in accordance with the present invention. In the illustrated embodiment of the invention, the fasteners 20 are formed of one piece of biocompatible material, specifically, anodized titanium. However, the fasteners 20 could be formed of a different material if desired. For example, the fasteners 20 could be formed of stainless steel.

The fasteners 20 have inner end or mounting sections 22 which engage bone in a vertebra 16 to fixedly mount the fasteners in the vertebra. Although only a pair of fasteners 20 have been shown in FIG. 1, it should be understood that there are additional fasteners 20 connected with adjacent vertebrae 16 of the spinal column 10.

Each of the retainer assemblies 12 and 14 (FIG. 1) includes a longitudinal member, such as a cylindrical rod 26 which extends along the spinal column 10. The rods 26 are made of a biocompatible material, such as stainless steel or titanium. Each of the rods 26 has a length which is sufficient to enable the rod to span at least two of the vertebrae 16 in the spinal column 10. Of course, the length of the rods 26 in any particular installation will depend upon the condition to be corrected and the number of vertebrae 16 to be held in a desired spatial relationship relative to each other by the retainer assemblies 12 and 14. The rods 26 may be bent to conform to a desired curvature of the spinal column 10 in all or any of the three possible anatomic planes.

Connector assemblies 30 interconnect the rods 26 and the fasteners 20. Each of the connector assemblies 30 includes a retainer member 32. Each of the retainer members 32 is provided with an opening through which one of the rods 26 extends. Each of the retainer members 32 has a second opening or slot 38 through which a retaining section 40 of a fastener 20 extends.

Retaining clamps 50 hold the retainer members 32 against movement relative to the fasteners 20. The retaining clamps 50 include internally threaded retainer nuts 52 which engage threads on the retaining sections 40 of the fasteners 20. Locknuts may be provided to clamp the retainer nuts 52 in place on the fasteners 20.

The distance between the rods 26 and the fasteners 20 can be varied while the rods 26 and fasteners are connected with the retainer members 32 and while the fasteners 20 remain stationary relative to the vertebrae 16. To enable temporary relative movement to occur between the rods 26 and fasteners 20, the slots 38 in the connector members 32 have an oblong configuration. Therefore, a vertebra 16 engaged by a fastener 20 can be moved either toward or away from a rod 26 which is being held substantially stationary.

The general construction of the retainer assemblies 12 is similar to the construction of retainer assemblies disclosed in U.S. Pat. No. 5,129,900. However, it should be understood that the retainer assemblies 12 and 14 could have any desired construction. For example, the retainer assemblies 12 and 14 could be constructed in the manner disclosed in U.S. Pat. No. 4,854,311 or U.S. Pat. No. 5,024,213 if desired.

The fastener 20, which is constructed in accordance with the present invention, has a mounting section 22 with a helical external thread convolution 60 (FIGS. 2 and 3) which engages one of the vertebrae 16 (FIG. 1). The thread convolution 60 engages the bone in vertebra 16. The retaining section 40 (FIGS. 2 and 3) has a helical external thread convolution 62 which engages one of the retainer nuts 52.

A circular intermediate or head section 64 is disposed between the mounting section 22 and retaining section 40. The intermediate section 64 projects radially outward of the mounting section 22 and retaining section 40. The external thread convolutions 60 and 62, mounting section 22, retaining section 40, and intermediate section 64 all have central axes which are coincident with a central axis of the fastener 20.

Fastener—Mounting and Intermediate Sections

The mounting section 22 of the fastener 20 has the external thread convolution 60 to connect the fastener with a vertebra 16. The external thread convolution 60 is a coarse helical thread convolution. A six (6) degree taper or runout is provided at an upper (as viewed in FIG. 3) end portion 68 of the external thread convolution 60. The external thread convolution 60 may have a configuration similar to the configuration disclosed in U.S. Pat. No. 4,854,311. However, it should be understood that the external thread convolution 60 could have any desired configuration. It is believed that a relatively coarse thread convolution will probably be preferred in order to provide secure engagement with bone in a vertebra 16.

The intermediate section 64 (FIG. 3) is disposed in a coaxial relationship with the mounting section 22 and retaining section 40. The intermediate section 64 has a generally circular cross sectional configuration. The intermediate section 64 includes a lower side surface 72 which forms a portion of a cone.

The conical side surface 72 has a central axis which is coincident with the central axis of the fastener 20. The side surface 72 flares radially outward and axially upward (as viewed in FIG. 3) from the outer end portion 68 of the mounting section 22 toward the retaining section 40. It is contemplated that the side surface 72 may be pressed against a vertebra 16 when the fastener 20 is used to retain the vertebrae in a desired spatial relationship.

The intermediate section 64 also includes a cylindrical side surface 74 which is disposed in a coaxial relationship with the conical side surface 72 and the mounting section 22. A pair of identical recesses 78 and 80 (FIG. 2) are formed in diametrically opposite portions of the intermediate section 64. The recesses 78 and 80 have generally rectangular (FIG. 4) open end portions which face upwardly (as viewed in FIG. 2) toward the retaining section 40. The recess 78 (FIG. 3) has an arcuate bottom surface 82 with a center of curvature disposed on a radius of the cylindrical side surface 74. The recesses 78 and 80 are engageable by a suitable tool to rotate the mounting section 22 relative to a vertebra 16.

Fastener—Retaining Section Flats

The retaining section 40 (FIGS. 2 and 3) of the fastener 20 is formed as one piece with and is disposed in a coaxial relationship with the mounting section 22 and intermediate section 64. The external thread convolution 62 on the retaining section 40 is disposed in a coaxial relationship with the external thread convolution 60 on the mounting section 22. A retainer nut 52 (FIG. 1) engages the external thread convolution 62 on the retaining section 40 to hold the retainer member 32 against movement relative to the fastener 20.

In accordance with a feature of the present invention, parallel flats 88 and 90 (FIG. 4) are formed on opposite sides of the retaining section 40. The parallel flats 88 and 90 extend between axially opposite ends of the retaining section 40 (FIG. 2). The identical flats 88 and 90 engage parallel sides of the slot 38 (FIG. 1) in the retainer member 32 to block relative rotation between the fastener 20 and the retainer member 32.

The slot 38 in the retainer member 32 is sized so as to accommodate sliding adjustment between the retainer member 32 and fastener 20. Of course, when the retainer nut 52 is tightened, the retainer member 32 is securely clamped between the intermediate section 64 and the retainer nut to hold the retainer member against movement relative to the fastener 20.

The flats 88 and 90 (FIG. 4) are separated by a distance which is substantially equal to or greater than a root diameter of the external thread convolution 62. The external thread convolution 62 has helical flank surfaces 94 and 96 (FIG. 6) which intersect at a helical crest 98 and a helical root 100 of the external thread convolution 62. The external thread convolution 62 is formed in a cylindrical shank portion 104 of the retaining section 40.

In the illustrated embodiment of the retaining section 40, the distance between the flats 88 and 90 (FIG. 4) is equal to the root diameter of the external thread convolution 62. This results in the parallel flats 88 and 90 extending tangentially to the root 100 of the external thread convolution 62. Therefore, the minimum distance between the flats 88 and 90, that is, the distance as measured along a diametral axis perpendicular to the flats, is equal to the diameter of the root 100 of the external thread convolution 62.

By having the distance between the flats 88 and 90 (FIG. 4) equal to the root diameter of the external thread convolution 62, the shank portion 104 of the retaining section 90 is not weakened by removal of material to form the flats 88 and 90. In order to form the flats 88 and 90, only the material of the external thread convolution 62 is removed from the retaining section 40. This results in the strength of the shank portion 104 being substantially the same before and after the flats 88 and 90 are formed on the retaining section 40.

When the fastener 20 is being formed, the external thread convolution 62 is formed into the shank portion 104 of the retaining section 40. Thereafter, the flats 88 and 90 are formed. During formation of one embodiment of the fastener 20, the flats 88 and 90 were formed by machining the retaining section 40 to remove material from the external thread convolution 62. To form the flats 88 and 90, metal in the external thread convolution 62 was removed by a milling operation. However, the flats 88 and 90 could be formed by grinding if desired.

Figure 5:
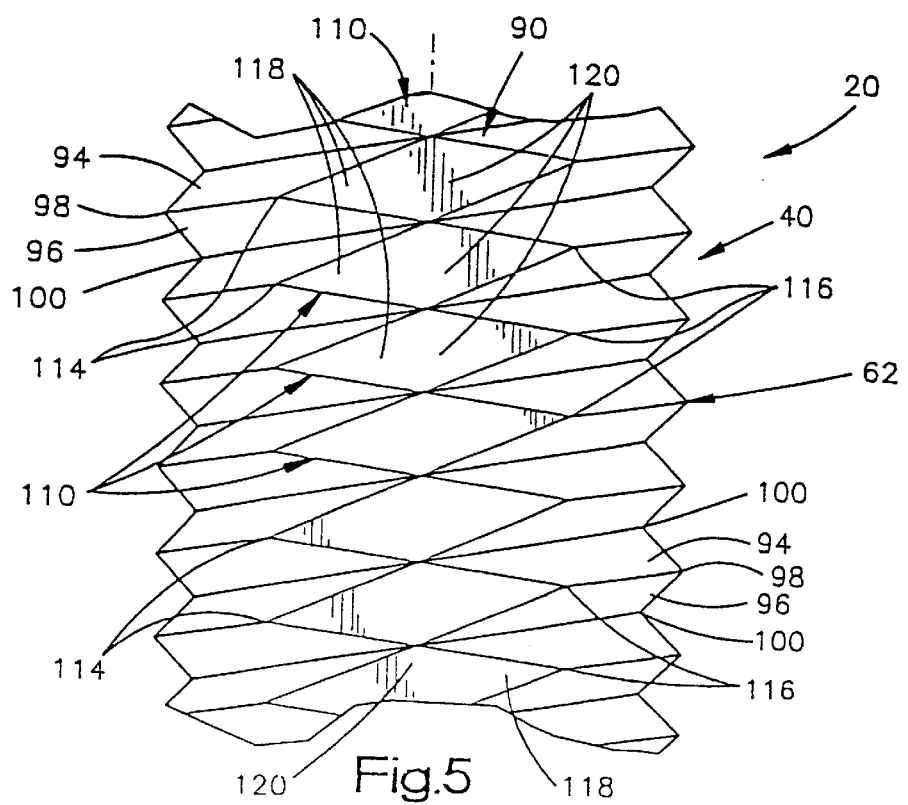
FIG. 5 is a fragmentary side elevational view, taken generally along the line 5—5 of FIG. 4, depicting the configuration of a flat formed on one side of the fastener of FIG. 2.

The parallel flats 88 and 90 extend from the intermediate section 64 to the upper (as viewed in FIG. 3) end of the retaining section 40. The parallel flats 88 and 90 have the same configuration. The configuration of the flat 90 is illustrated in FIG. 5. The flat 90 includes a plurality of generally diamond-shaped sections 110. The sections 110 all have the same configuration.

Each of the sections 110 of the flat 90 is formed by cutting away the material on one turn of the helical external thread convolution 62. The crest 98 of a turn of the external thread convolution 62 is interrupted at an edge of the flat 90. Therefore, each of the sections 110 of the flat 90 has pointed ends 114 and 116 (FIG. 5) where a flat surface 118 of the section 110 intersects the crest 98 of one of the turns of the helical external thread convolution 62.

Each of the sections 110 of the flat 90 has a relatively wide central portion 120. The flat surface 118 of the flat 90 is tangential to the root 100 (FIG. 5) of the external thread convolution 62 at the wide central portion 120 of each of the sections 110. At a line of tangency of the plane in which the flat 90 is disposed with the root diameter 100 of the thread convolution 62, there is a linear area where the sections 110 of the flat 90 intersect.

The crest 98 of each turn in the external thread convolution 62 is interrupted for the entire width of the flat 90, that is, for the distance between the pointed ends 114 and 116 of the section 110. However, the root 100 of the external thread convolution 62 is interrupted only at the line of tangency of the plane in which the flat 90 is disposed with the root 100 of the external thread convolution.

Each of the sections 110 of the flat 90 is formed by a flat surface. The flat surfaces 118 of the sections 110 extend between their pointed ends 114 and 116 and are disposed in a plane which extends parallel to a longitudinal central axis of the fastener 20 and parallel to a plane containing the flat 88 (FIG. 4). The pointed ends 114 and 116 are disposed at opposite edge portions of the flat 90. The opposite edge portions of the flat 90 extend parallel to the central axis of the retaining section 40.

If the spacing between the flats 88 and 90 is somewhat less than the diameter of the root 100 of the external thread convolution 62, the circumferential extent or width of the sections 110 of the flat 90 (FIG. 5) is increased. When this happens, the width of the area where the central portions 120 of the sections 110 intersect is increased. However, if the distance between the flats 88 and 90 is less than the diameter of the root 100 of the external thread convolution 62, material is removed from the shank portion 104 of the retaining section 40.

In order to maximize the strength of the retaining section 40, it is believed that it will probably be desired to have the minimum distance between the flats 88 and 90 at least as great as the diameter of the root 100 of the external thread convolution 62. However, there may be circumstances when the increased flat width obtained by having the distance between the flats 88 and 90 less than the diameter of the root 100 of the external thread convolution 62 justifies decreasing the strength of the shank portion 104 of the retaining section 40.

Fastener—Retaining Section Drive

A drive recess 130 (FIGS. 2, 3 and 6) is formed in the outer or upper end portion of the retaining section 40. The drive recess 130 receives a drive tool (not shown). Force is applied to the drive tool to rotate the fastener 20 relative to the vertebra 16.

Figure 6:
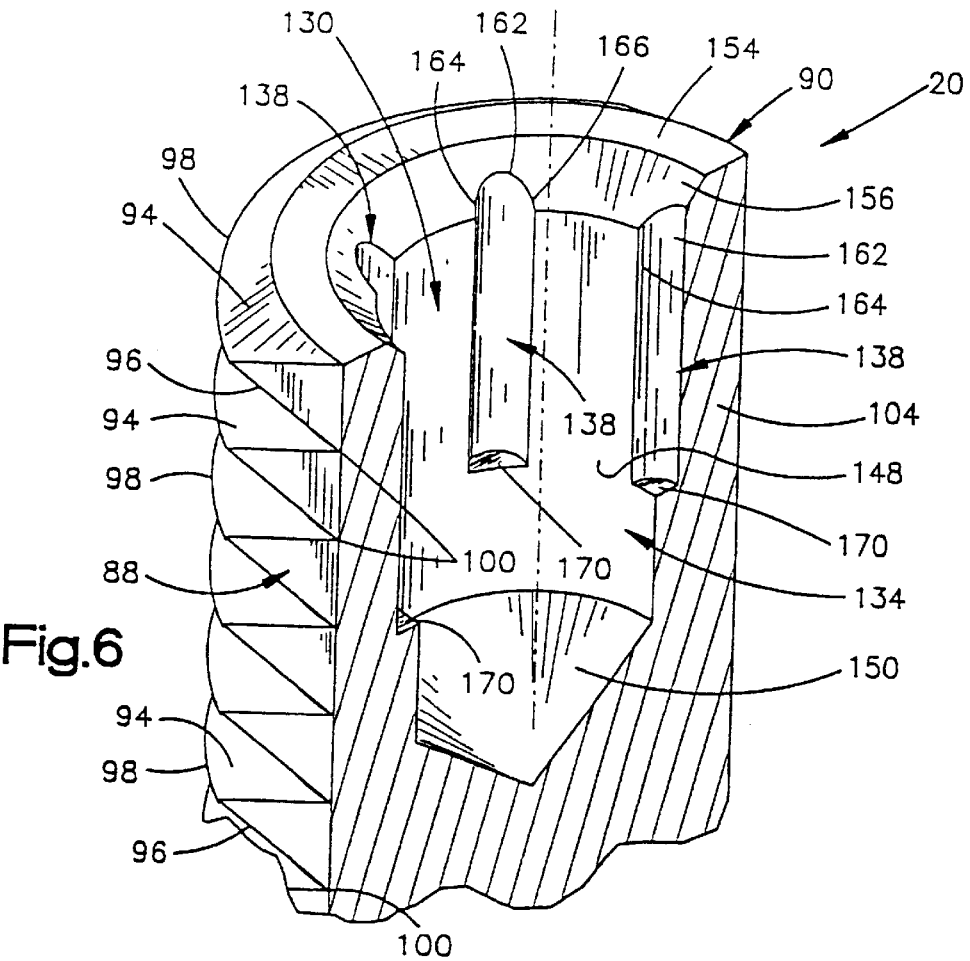
FIG. 6 is a fragmentary pictorial sectional view, taken generally along the line 6—6 of FIG. 4, illustrating the construction of a drive recess in the retaining section of the fastener.

The drive recess 130 includes a cylindrical main portion 134 and a plurality of arcuate corner portions 138 (FIGS. 4 and 6). The arcuate corner portions 138 receive projecting portions of the drive tool. Force is transmitted from the drive tool to the arcuate corner portions 138 of the recess 130 to rotate the fastener 20 relative to a vertebra 16.

In accordance with a feature of the present invention, the arcuate corner portions 138 are offset from a plane which contains the center line of the fastener 20 and extends perpendicular to the flats 88 and 90. The plane which contains the center line of the fastener 20 and extends perpendicular to the flats 88 and 90 is a diametral plane of the fastener and has been indicated at 144 in FIG. 4.

By having the arcuate corner portions 138 offset from the diametral plane 144, the corner portions are disposed in a portion of the shank where the external thread convolution 62 has not been interrupted to form the flats 88 and 90. This tends to maximize the strength of the shank portion 104 at the locations where the arcuate corner portions 138 are formed. The strength of the shank portion 104 is also promoted by the stress minimizing arcuate configuration of the corner portions 138. Therefore, the corner portions 138 are capable of transmitting relatively large driving forces (torque) without fracturing of the material of the shank portion 104 adjacent to the corner portions 138.

A generally cylindrical main portion 134 (FIG. 6) of the drive recess 130 includes a cylindrical side wall 148 and a conical bottom wall 150. The cylindrical side wall 148 is connected with a flat annular end surface 154 on the shank portion 104 by a sloping countersink surface 156 which is formed as a portion of a cone. The cylindrical side wall 148, bottom wall 150 and countersink surface 156 of the drive recess 130 are disposed in a coaxial relationship with a longitudinal central axis of the retaining section 40 and fastener 20.

The arcuate corner portions 138 (FIG. 4) of the drive recess 130 extend radially outward from the cylindrical side wall 148. The arcuate corner portions 138 are disposed in a circular array about an axis which is coincident with the longitudinal central axis of the retaining section 40 and fastener 20. The arcuate corner portions 138 are spaced equal arcuate distances apart about the central axis of the fastener 20.

In the illustrated embodiment of the invention, there are six arcuate corner portions 138 (FIG. 4) which are spaced 60 degrees apart. It should be noted that the two corner portions 138 which are closest to the flat 88 are both offset by 30 degrees from the diametral plane 144 through the center of the flat 88. Similarly, the corner portions 138 which are closest to the flat 90 are both offset by 30 degrees from the portion of the plane 144 which extends through the center of the flat 90. Of course, if a different number of corner portions 138 were provided in the drive recess 130, the arcuate distance between the corner portions would be different and the arcuate distance by which the corner portions are offset from the plane 144 would be different.

The corner portions 138 all have the same configuration. Each of the corner portions 138 includes an arcuate, radially outwardly projecting, side surface 162 (FIG. 6). Each of the arcuate side surfaces 162 has a longitudinal central axis which extends parallel to the coincident central axes of the drive recess 130 and the retaining section 40. The arcuate side surfaces 162 have a continuously curving configuration and are free of stress inducing discontinuities which would result from sharply defined corner portions.

As is perhaps best seen in FIG. 6, each of the corner portions 138 has a pair of flat side surfaces 164 and 166 which flare outwardly from the arcuate side surface 162. The flat side surfaces 164 and 166 extend between an arcuate side surface 162 and the cylindrical side wall 148 of the main portion 134 of the drive recess 130. Each of the corner portions 138 has a flat inner end surface 170 (FIG. 6) which extends radially outward from the cylindrical side wall 148 of the drive recess 130. Diametrically opposite corner portions 138 are spaced apart by a distance which is less than the distance between the flats 88 and 90.

A drive tool (not shown) has an end portion which fits into the drive recess 130. The drive tool has a plurality of radially outwardly extending projections which are configured for mating engagement with the corner portions 138. When the drive tool is inserted into the recess 130, the drive tool mates with all six of the corner portions 138. Upon application of torque to the drive tool, force is transmitted to all six of the corner portions 138. This force rotates the fastener 20 relative to the vertebra 16.

Although one specific configuration for the drive recess 130 has been illustrated in FIGS. 4 and 6, it is contemplated that the drive recess could have a different configuration if desired. For example, the drive recess 130 could have radially inwardly curving side walls disposed between the corner potions 138. The radially inwardly curving side walls between the corner portions 138 would form lobes which would increase the extent of engagement of the fastener 20 with the drive tool.

Fastener—Second Embodiment

Figure 7:
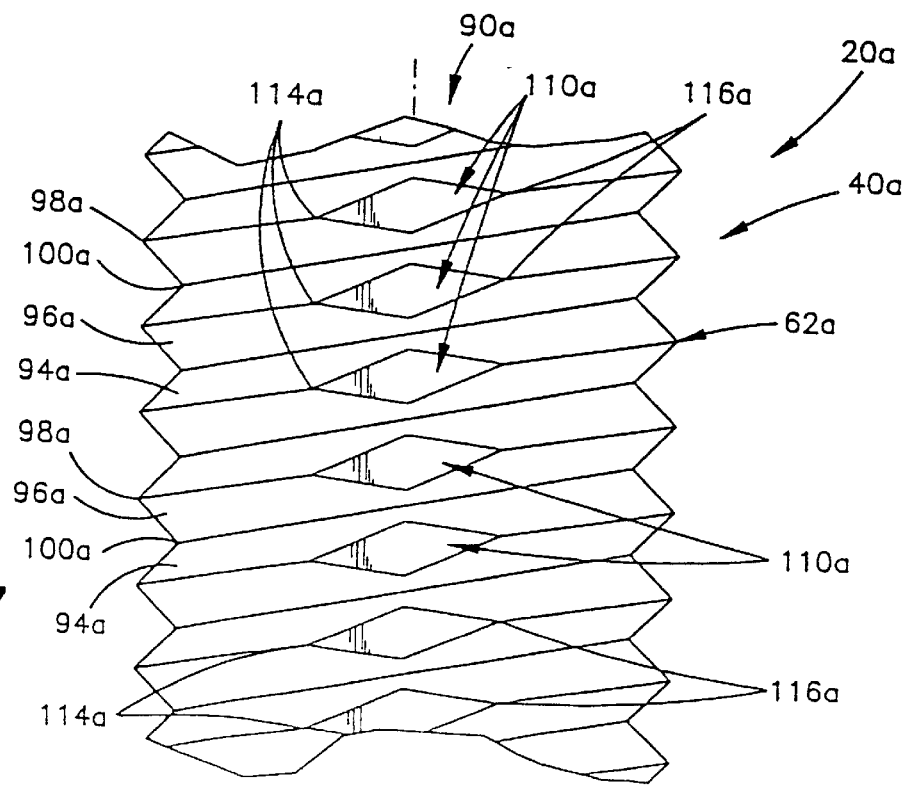
FIG. 7 is a fragmentary illustration, generally similar to FIG. 5, depicting the configuration of a second embodiment of a flat formed on one side of a retaining section of a fastener.

In the embodiment of the fastener 20 illustrated in FIGS. 1–6, the flats 88 and 90 extend tangentially to the root 100 of the external thread convolution 62. Thus, in the embodiment of the fastener 20 illustrated in FIGS. 1–6, the distance between the flats 88 and 90 is equal to the root diameter of the external thread convolution 62. In the embodiment of the invention illustrated in FIG. 7, the distance between the flats on the retaining section of the fastener is greater than the root diameter of the thread convolution. Since the embodiment of the invention illustrated in FIG. 7 is generally similar to the embodiment of the invention illustrated in FIGS. 1–6, similar numerals will be utilized to designate similar components, the suffix letter "a" being associated with the numerals of FIG. 7 in order to avoid confusion.

A fastener 20a has the same general construction as the fastener 20 of FIGS. 2 and 3. The fastener 20a includes a retaining section 40a having a helical external thread convolution 62a. The fastener 20a also has a mounting section and intermediate section (not shown) corresponding to the mounting and intermediate sections 22 and 64 on the fastener 20 (FIG. 2).

In accordance with a feature of this embodiment of the invention, a flat 90a (FIG. 7) on the retaining section 40a is spaced from the central axis of the fastener 20a by a radial distance which is greater than the radius of a root 100a of the external thread convolution 62a. Thus, the distance between the parallel flats on the retaining section 40a is greater than the root diameter of the external thread convolution 62a. This results in the external thread convolution 62a having an uninterrupted helical root 100a. Although the flat 90a does not interrupt the root 100a of the external thread 62a, the flat 90a interrupts the crest 98a of the external thread 62a.

Since the flats on the retaining section 40a are spaced apart by a distance which is greater than the root diameter of the helical external thread convolution 62a, a portion of the thread convolution extends across each of the flats. Thus, the sections 110a of the flat 90a are separated by grooves. These grooves include the root 100a of the external thread convolution 62a. The root 100a of the external thread convolution extends across the flat 90a.

The flat 90a was formed by cutting away material from the flanks 94a and 96a of the external thread convolution 62a. This results in the formation of a plurality of spaced apart sections 110a. The sections 110a extend between pointed ends 114a and 116a. The distance between the pointed ends 114a and 116a is less than the distance between the pointed ends 114 and 116 of the sections 110 of the flat 90 of FIG. 5. Therefore, the sections 110a of the flat 90a of FIG. 7 have a smaller width than the sections 110 of the flat 90 (FIG. 5).

Although only the flat 90a is illustrated in FIG. 7, it should be understood that the fastener 20a has a second flat, corresponding to the flat 88 of FIG. 4, which extends parallel to the flat 90a. The second flat, which extends parallel to the flat 90a, has the same configuration as the flat 90a. The root 100a of the thread convolution 62a extends across the second flat which extends parallel to the flat 90a.

Conclusion

The present invention provides a new and improved fastener 20 to retain vertebrae 16 in a desired spatial relationship. The fastener 20 includes a mounting section 22 having an external thread 60 which engages a vertebra. The fastener has a retaining section 40. The retaining section 40 may have a pair of parallel flats 88 and 90 disposed on opposite sides of the retaining section. In addition, the retaining section 40 may have a drive recess 130 disposed between the flats 88 and 90 at end of the retaining section. The drive recess 130 has a plurality of arcuate corner portions 138 which are offset from a plane 144 containing a longitudinal central axis of the retaining section 40 and extending perpendicular to the flats 88 and 90.

An external thread 62 may be provided around the retaining section 40 to engage an internal thread on a retaining element 52. The flats 88 and 90 on the retaining section 40 may be spaced apart by a distance which is at least as great as a root diameter 100 of the external thread 62 on the retaining section.

Having described the invention, the following is claimed:

1. A fastener for use in retaining vertebrae in a desired spatial relationship, said fastener comprising a first section having first external thread means for engaging a vertebra, a second section connected with said first section and having a pair of parallel flats disposed on opposite sides of said second section, said second section having second external thread means to engage an internal thread on a retaining element, said flats being spaced apart by a distance which is at least as great as a root diameter of said second external thread means, said second external thread means having a root diameter which is less than the distance between said flats so that a root portion of said second external thread means extends across said flats.

2. A fastener as set forth in claim 1 wherein each of said flats has first and second edge portions which extend parallel to a central axis of said second section, said second external thread means having a crest portion which is interrupted at said first and second edge portions of said flats.

3. A fastener as set forth in claim 1 wherein said second section of said fastener further includes a driving recess having a plurality of corner portions which receive force to effect rotation of said fastener relative to a vertebra engaged by said first section of said fastener.

4. A fastener as set forth in claim 3 wherein each of said corner portions has an arcuate configuration and is offset from a plane containing a longitudinal central axis of said second section and extending perpendicular to said flats.

5. A fastener as set forth in claim 1 wherein each flat of said pair of parallel flats includes a plurality of spaced apart sections, each section of said plurality of sections having a pair of end portions where a surface of the flat intersects a crest of said second external thread means.

6. A fastener as set forth in claim 1 wherein each flat of said pair of flats includes a plurality of spaced apart sections, each section of said plurality of sections having a wide central potion which is adjacent to the root portion of said second external thread means, each section of said plurality of sections having a pair of end portions which taper to the crest of said second external thread means.

7. A fastener as set forth in claim 1 wherein the root portion of said second external thread means is uninterrupted and extends across each of said flats.

8. A fastener for use in retaining vertebrae in a desired spatial relationship, said fastener comprising a first section having first external thread means for threaded engagement with a vertebra, a second section connected with said first section and having a pair of parallel flats disposed on opposite sides of said second section and a driving recess disposed in one end of said second section between said flats, said driving recess having a plurality of arcuate corner portions to receive force to effect rotation of said fastener relative to a vertebra engaged by said first section, said arcuate corner portions of said driving recess being offset from a plane containing a longitudinal central axis of said second section and extending perpendicular to said flats, and second external thread means on said second section to engage an internal thread on a retaining element, said second external thread means having a root diameter which is no greater than a minimum distance between said flats.

9. A fastener as set forth in claim 8 wherein said first and second sections have coincident central axes.

10. A fastener as set forth in claim 8 further including an intermediate section disposed between said first and second sections, said intermediate section having a circular outer side surface which flares axially and radially outward in a direction away from said first section toward said second section.

11. A fastener as set forth in claim 8 wherein said driving recess includes a cylindrical main wall having a central axis which is coincident with a central axis of said second section, each of said arcuate corner portions includes an arcuate side surface having a longitudinal axis which extends parallel to the central axis of said cylindrical main wall.

12. A fastener as set forth in claim 8 wherein each of said arcuate corner portions has a longitudinal central axis which is disposed in a plane which contains a longitudinal central axis of said second section.

13. A fastener as set forth in claim 8 wherein each flat of said pair of parallel flats includes a plurality of sections, each one of said sections of said plurality of sections having a pair of end portions where a flat surface of each one of said sections of said plurality of sections intersects a crest of said second external thread means.

14. A fastener as set forth in claim 8 wherein each flat of said pair of flats includes a plurality of sections, each section of said plurality of sections having a wide central portion which is tangential to the root diameter of said second external thread means.

15. A fastener as set forth in claim 8 wherein each flat of said pair of flats includes a plurality of sections which are spaced apart from adjacent sections.

\* \* \* \* \*